(12) United States Patent
Brown

(10) Patent No.: US 6,852,123 B2
(45) Date of Patent: Feb. 8, 2005

(54) MICRO STRUCTURE STENT CONFIGURATIONS

(75) Inventor: Brian J. Brown, Hanover, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 220 days.

(21) Appl. No.: 10/101,262

(22) Filed: Mar. 18, 2002

(65) Prior Publication Data
US 2002/0138132 A1 Sep. 26, 2002

Related U.S. Application Data

(62) Division of application No. 09/437,049, filed on Nov. 9, 1999, now Pat. No. 6,428,569.

(51) Int. Cl.[7] .................................................. A61F 2/06
(52) U.S. Cl. ..................................................... 623/1.15
(58) Field of Search ............................. 623/1.15, 1.16, 623/1.27, 1.35, 1.44, 1.17, 1.1; 606/191, 195, 198

(56) References Cited

U.S. PATENT DOCUMENTS

| | | | | |
|---|---|---|---|---|
| 6,120,535 A | * | 9/2000 | McDonald et al. | 623/1.39 |
| 6,325,823 B1 | * | 12/2001 | Horzewski et al. | 623/1.16 |
| 6,331,191 B1 | * | 12/2001 | Chobotov | 623/1.44 |
| 6,352,561 B1 | * | 3/2002 | Leopold et al. | 623/1.23 |
| 6,428,569 B1 | | 8/2002 | Brown | |

* cited by examiner

Primary Examiner—Kevin T. Truong
(74) Attorney, Agent, or Firm—Vidas, Arrett & Steinkraus, P.A.

(57) ABSTRACT

Fine structure stents physiologically acceptable to the body.

11 Claims, 2 Drawing Sheets

MICRO STRUCTURE STENT CONFIGURATIONS

RELATED APPLICATIONS

This application is a continuation of U.S. patent application Ser. No. 09/437,049 filed Nov. 9, 1999 now U.S. Pat. No. 6,428,569, the content of which is incorporated herein by reference.

BACKGROUND OF THE INVENTION

This invention relates to medical stents. Medical stents are well know for use in opening and reinforcing the interior wall of blood vessels and other body conduits.

Stents are generally tubular in configuration and radially expandable. They may be of the self-expanding type or they may be mechanically expandable with an outward pressure applied to the stent. Typically, the later type stents are expanded by means of an interiorly positioned balloon. Stents may be made of various materials such as plastic or metal. Presently, metal is the material of choice.

This invention is specifically concerned with stents in the form of a closed cylinder which is made up of a plurality of struts, the struts being deformed either permanently or otherwise upon expansion of the stent.

To-date, stents, particularly coronary stents, have been made up of elements that are relatively large and of the following order:

strut width 0.004 inches 0.008 inches strut thickness 0.002 inches 0.007 inches largest dimension of opening between struts 0.100 inches 0.200 inches These dimensions and all other dimensions referred to herein after refer to the stent in its expanded state.

The basic idea behind the present invention is to provide a stent of fine structure (micro structure) that provides adequate vessel support but the openings therein are so small that the stent creates minimal disruption of the vessel surface and is so fine that it is for all practical purposes "invisible" to the body in which it is implanted and to the body constituents such as blood flow.

An analogous example is a window screen, the idea being to provide a screen (stent) to support a vessel but which is from the stand point of the various physiological aspects of the body so fine as to be effectively "invisible" and for all practical purposes can then be said to be considered by the body as being nonexistent. There does exist in the art one example of an ultra thin micro porous nickel titanium foil which is rolled in the fashion of a jelly roll to provide a self-expanding stent. Self-expansion is provided by the natural unrolling tendency of the tightly wound stent following its implantation. However, this type of stent has not been widely acceptable and differs from the stents of the present invention in that no strut deformation occurs with respect to the elements making up the foil or screen of the ultra thin micro porous jelly roll type stent. Cardiovascular Dynamics, Inc., has published material concerning the "jelly roll" stent.

BRIEF SUMMARY OF THE INVENTION

In contrast to the above-identified prior art, this invention provides stents of closed cylindrical construction in which expansion is accompanied by deformation of the strut structure making up the body of the stent. As already pointed out, the term deformation is meant to include other deformation in addition to permanent deformation as used in the metallurgical sense. In accordance with this invention a suitable micro structure design can be obtained by constructing a stent having a reduction ratio as compared to current coronary stents of 4:1 to 10:1. Note with reference to ratio reduction—current dimensions are thereby reduced by a factor of about 4–10.

Even more specifically, micro structure stents in accordance with the present invention will preferably have about the following dimensions:

strut width 0.00025–0.002 inches strut thickness 0.00025–0.004 inches maximum PIN opening 0.002–0.020 inches diameter (current stent designs typically have a maximum PIN opening of around 0.025 inches to 0.050 inches in diameter).

The term "maximum PIN opening" is used herein to describe micro openings in which the dimensions specify the largest which can be passed through the cell opening. This applies as noted above to the expanded stent configuration. Typically, as a stent is expanded to larger diameters, the opening becomes larger. It is believed that using a maximum PIN opening specification that the concept of the present invention may be more readily applicable to stents of either open or closed cell geometries.

The preferred stents having a micro structure in accordance with the present invention will also have a wall thickness of up to 0.004 inches which is not required according to the invention but provides adequate radiopacity and handling characteristics in the stent structure.

In addition to directly forming a micro structure in the wall of a stent, this invention may be accomplished by providing a stent within a stent wherein both stents, even though having larger openings than would be characterized as providing micro structure, may in fact provide micro structure by control of the registration of the openings in the stents as is more fully described below.

The stent within a stent combination leads to other embodiments of the invention which are also described more fully below.

As with any stent design, many different designs are possible with respect to features such as flexibility, etc. The geometries which are shown hereinbelow are included only for illustrative purposes.

BRIEF DESCRIPTION OF THE DRAWING(S)

DESCRIPTION OF THE PREFERRED EMBODIMENTS

This invention in contrast to the prior art jelly roll structure suggests that micro porous stents should be provided which have a deformable structure. Generally, this is meant that the deformable struts of both self-expanding and mechanically-expandable stents already known in the art should be provided with micro porous structure. The fabrication of such stents is typically from flat sheet which is rolled then welded into a cylinder or from tubular stock.

Figure 1:
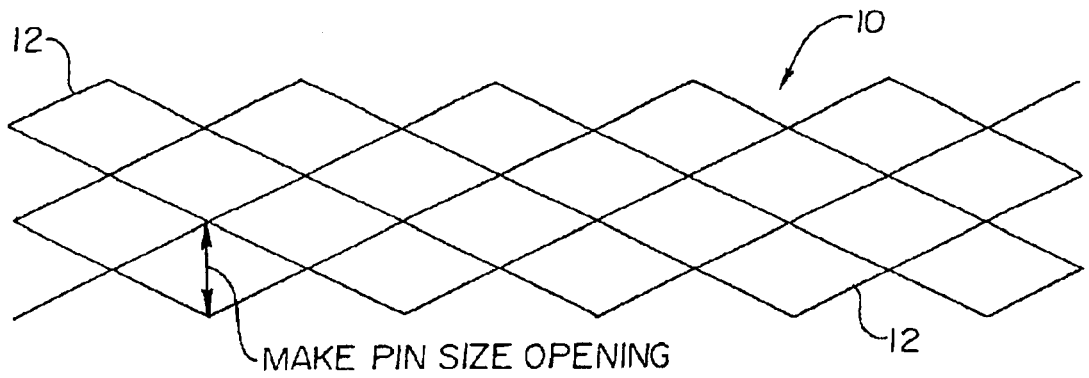
FIG. 1 is a schematic fragment showing a micro structure stent of the invention.

A first way involves simply making the struts and the openings of the stent extremely small. Such a stent would be comprised of a plurality of interconnected deformable struts arranged with respect to each other to provide a micro structure which facilitates support with a minimal disruption in the vessel of a body, the micro structure being characterized, after expansion, by about the following dimensions or smaller.

strut width 0.00025–0.002 inches
strut thickness 0.00025–0.004 inches
maximum PIN opening 0.002–0.20 inches Having reference to FIG. 1, there is shown in fragment a portion of a stent 10 of closed cell geometry in schematic form. This stent could be taken to be formed of wire or wires 12 into a cylindrical configuration to form the stent 10. On the other hand, the struts formed by wire 12 could also be manufactured by laser cutting struts 12 from tubular stock of an appropriate diameter.

Figure 2:
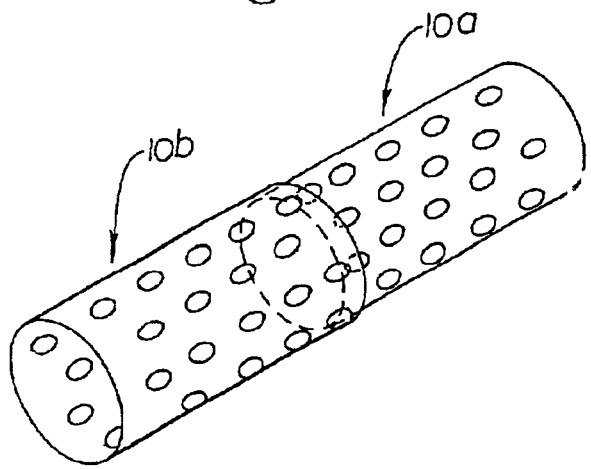
FIGS. 2 and 3 are schematic showings of a stent within a stent according to this invention.
Figure 3:
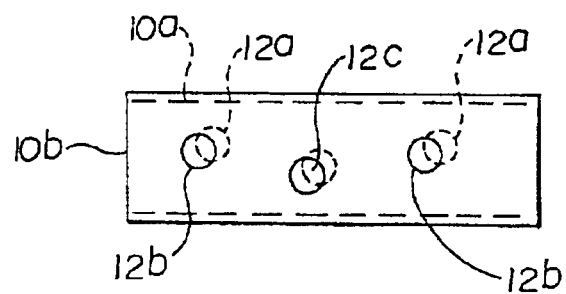

A second way to achieve micro structure in a stent involves the combination of one stent within another stent (slidably interfitted) in which the openings in the stents are mismatched or out of register relative to each other to provide an overall opening which is smaller than either of any of the two registered openings. That is, the openings do not exactly correspond with each other and are not exactly aligned with respect to each other. In such a situation each of the stents may have openings over a wide range of sizes which may or may not be individually micro porous but together in registration provide micro porous openings. However, when one stent is placed within the other and the openings are positioned out of alignment with respect to each other it can be seen that smaller openings thorough the combined stents can be achieved and can become micro porous even when the original openings are not. Such a structure is shown in FIGS. 2 and 3 in which an apertured stent 10a is being slidably interfitted with an apertured stent 10b. As can be seen in FIG. 3 when the two stents are completely combined, openings 12a in stent 10a when out of register with openings 12b in stent 10b will provide openings 12c of markedly smaller size than either of the openings 12a or 12b.

Such a combination may even include a third stent within the second stent and so forth. Each stent in such a case would be fabricated independently following which the stents would be slidably interfitted one into the other to provide the overall combination.

The combined stents if tightly fit together would not necessarily require any sort of fastening means. However, the stents could be joined as by welding or by the use of adhesives. If adhesives are used, the adhesives could be biodegradable or even contain a drug eluting material.

The primary purpose of using the second approach for achieving micro structure is based on the fact that it is easier to make fine holes through thin metal than through thick metal. Of course, for flexibility considerations, each interfitted stent will preferably be as thin as possible.

This concept of a stent within a stent has other ramifications as well. By fabricating each stent individually, one can achieve finer detail than if thicker material is used. A limiting factor in most fabrication processes is depth to width ratio. With a thin working layer the level of detail can be much finer.

Thus, even if one does not wish to fabricate a micro porous stent it may be advantageous to utilize the stent within a stent concept to provide stents which, although registered with each other in so far as the openings therein are concerned, would provide a combination having a finer level of detail in the opening configuration.

Thus, the concept of a stent within a stent, when viewed broadly, would not necessarily be limited to micro structure stents or to deformable stents but rather would be applicable broadly to stents in which it is desired to obtain finer detail in the configuration of the pattern making up the openings within the stent. This in addition to the primary purpose of the subject invention in which the combination of multiple layers, i.e., a stent within a stent to achieve stent strength and to create micro porous openings due to mismatch or lack of registration of the cell openings in each layer.

Presently, physicians sometimes implant a first stent and then implant a second stent within the first stent. An embodiment of this invention contemplates a further development of this practice by providing a stent within a stent combination already for implant. Thus the two stents may be implanted simultaneously. Several advantages are attendant with such a combination.

The prior practice of implanting first one stent followed by the implantation of a second stent within the first stent makes use of presently available stents of ordinary wall thickness. Such an implanted stent within a stent results in a relatively thick wall structure which is detrimental to flexibility and also to flow dynamics within the vessel.

By providing a combination stent within a stent prior to implantation, one may combine stents purposely made of less than ordinary wall thickness to achieve thinner overall stent structure which will exhibit improved overall performance such as:

Uniform vessel coverage
less gapping
small cell openings improved flexibility
layers can move relative to each other customized strength provided by adding or subtracting layers of stent.

Figure 4:
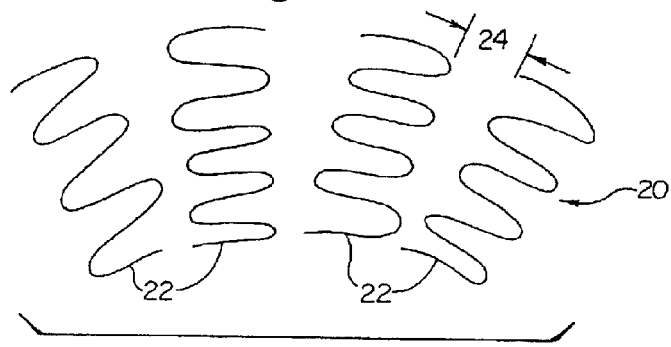
FIG. 4 is a schematic showing of a section of a stent made up of serpentine annular rings, the stent being bent.

For example, referring now to FIG. 4, a schematic showing of a well known type of stent configuration, generally indicated at 20, made up of a series of serpentine annular rings 22 is shown. As can be seen in FIG. 4, when the stent is bent to accommodate vessel curvature, gaps 24 enlarge.

Figure 5:
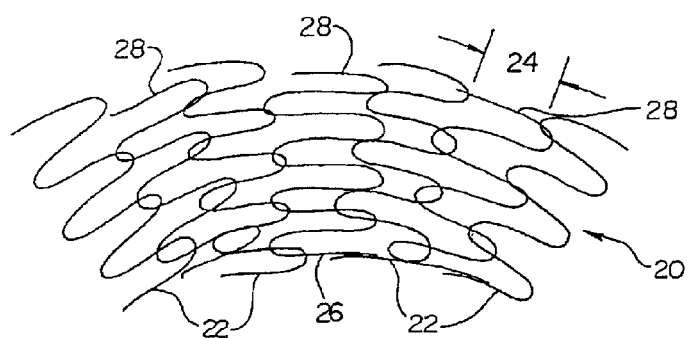
FIG. 5 is a schematic showing of a stent similar to that of FIG. 4 but including an inner stent arranged according to this invention.

Referring now to FIG. 5, a similar stent 20 is shown having the standard annular serpentine rings 22. However, included within the stent is a similar stent 26 arranged such that its rings 28 bridge the gaps 24 of the external stent 20 upon flexing or bending.

Figure 6:
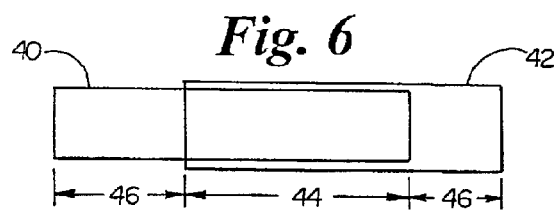
FIG. 6 is a schematic showing of a stent within a stent arranged according to this invention.

Customized stent strength may be accomplished by adding or subtracting stent layers. For example, refer to FIG. 6 which schematically shows a stent 40 partially within a stent 42. High strength is provided at region 44 where the two stents overlap and relatively low strength is provided at regions 46 where there is but a single stent structure. Such an arrangement provides a stent with soft ends.

Figure 7:
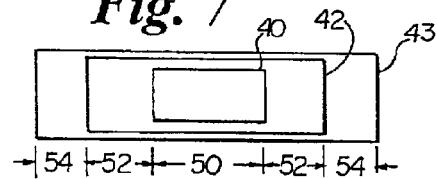
FIG. 7 is a schematic showing of three stents arranged within each other according to this invention.

Referring now to FIG. 7, a triple stent 40 within a stent 42 within a stent 43 is shown to provide three layers in region 50, two layers in regions 52 and a single layer in regions 54, thus providing three regions of different relative strength. Various other arrangements are available.

Figure 8:
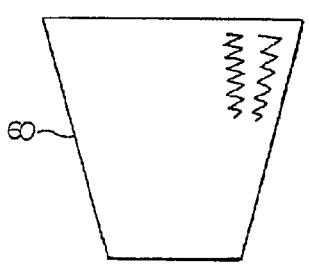
FIGS. 8–10 are schematic showings of another embodiment of the invention for providing multiple layer arrangements in a stent.
Figure 9:
Figure 10:
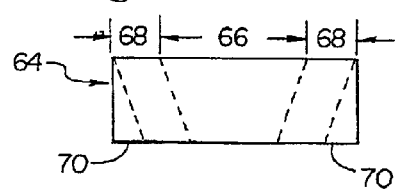

Lastly, variations in layers may be accomplished by rolling up a generally triangular shaped piece of metal sheet 60 shown in FIG. 8 to form a cylinder 62 indicated in FIG. 9 which has in fact regions of various layers as shown in FIG. 10. In FIG. 10 it can be seen that, when rolled up, sheet 60 provides a cylindrical stent structure 64 having more layers in the mid regions 66 and successively fewer layers in regions 68 and even fewer in region 70.

The above examples and disclosure are intended to be illustrative and not exhaustive. These examples and description will suggest any variations and alternatives to one of ordinary skill in the art. All such alternatives and variations are intended to be included within the scope of the attached claims. Those familiar with the art may recognize other equivalents to the specific embodiments described herein which equivalents are also intended to be encompassed by the claims attached hereto.

What is claimed is:

1. In combination, a first stent positioned internally of a second stent for simultaneous implantation, the second stent disposed directly about the first stent, the second stent being at least partially constructed of a self-expanding material and having a thickness of no more than about 50 microns.

2. The combinations of claim 1 wherein the first stent is only partially within the second stent.

3. The combination of claim 1 wherein the first stent and the second stent comprise annular segments, the first stent arranged within the second stent such that its annular segments bridge gaps between the annular segments of the second stent.

4. A variable strength stent having a first end and a second end, the stent comprising an inner stent layer and an outer stent layer, at least a portion of the outer stent layer disposed directly about at least a portion of the inner stent layer, the outer stent layer comprising a stent wall having a plurality of openings therethrough, the outer stent layer comprising a stent wall having a thickness of no more than about 50 microns, the outer stent layer being constructed of nickel-titanium.

5. The stent of claim 4 wherein the inner stent layer is formed of a plurality of serpentine rings.

6. The stent of claim 4 wherein the inner stent layer extends to the first or second end of the stent.

7. The stent of claim 4 wherein the inner stent layer does not extend to the first end of the stent and does not extend to the second end of the stent.

8. The stent of claim 4 wherein one end of the stent has a larger diameter than the other end of the stent.

9. The stent of claim 4 wherein both ends of the stent are of the same diameter.

10. The stent of claim 4 wherein the inner and outer stent layers fit tightly together.

11. The stent of claim 4 wherein the inner and outer stent layers are bonded to one another.

* * * * *